US012508402B2

(12) United States Patent
Yamamoto et al.

(10) Patent No.: US 12,508,402 B2
(45) Date of Patent: Dec. 30, 2025

(54) CATHETER ASSEMBLY

(71) Applicant: TERUMO KABUSHIKI KAISHA, Tokyo (JP)

(72) Inventors: Shota Yamamoto, Mitaka (JP); Shinnosuke Yamashita, Ljubljana (SI)

(73) Assignee: TERUMO KABUSHIKI KAISHA, Tokyo (JP)

( * ) Notice: Subject to any disclaimer, the term of this patent is extended or adjusted under 35 U.S.C. 154(b) by 922 days.

(21) Appl. No.: 17/408,336

(22) Filed: Aug. 20, 2021

(65) Prior Publication Data

US 2021/0379337 A1 Dec. 9, 2021

Related U.S. Application Data

(63) Continuation of application No. PCT/JP2020/010601, filed on Mar. 11, 2020.

(30) Foreign Application Priority Data

Mar. 28, 2019 (JP) ................................ 2019-063152

(51) Int. Cl.
*A61M 25/06* (2006.01)
*A61M 25/00* (2006.01)

(52) U.S. Cl.
CPC ........ *A61M 25/06* (2013.01); *A61M 25/0017* (2013.01); *A61M 25/0075* (2013.01); *A61M 25/0097* (2013.01)

(58) Field of Classification Search
CPC .......... A61M 25/0075; A61M 25/0097; A61M 2025/0018
See application file for complete search history.

(56) References Cited

U.S. PATENT DOCUMENTS 7,396,346 B2 7/2008 Nakajima
7,469,458 B1 12/2008 Starnes
(Continued)

FOREIGN PATENT DOCUMENTS

EP 1 911 485 B1 9/2009
EP 2 310 080 A1 4/2011
(Continued)

OTHER PUBLICATIONS

Extended European Search Report on EP 20777837.4 dated Apr. 19, 2022 (9 pages).
(Continued)

*Primary Examiner* — Courtney B Fredrickson
*Assistant Examiner* — Kayla M. Turkowski
(74) *Attorney, Agent, or Firm* — Foley & Lardner LLP

(57) ABSTRACT

A catheter assembly includes: an inner needle configured to puncture a living body; a catheter configured to allow the inner needle to be inserted therethrough; a catheter hub located at a proximal end of the catheter; a valve body located in an internal space of the catheter hub; an opening member located on a proximal side of the valve body, the opening member comprising: a cylindrical barrel portion, a neck portion extending from a distal end of the barrel portion, wherein a diameter of the neck portion is smaller than a diameter of the cylindrical barrel portion, and a foot portion extending to a proximal side of the barrel portion, wherein the opening member is configured to move in a distal direction to open the valve body; and a movement inhibiting mechanism that resists movement of the opening member in the distal direction via a contact portion.

17 Claims, 13 Drawing Sheets

(56) References Cited

U.S. PATENT DOCUMENTS

| | | | |
|---|---|---|---|
| 7,670,317 | B2 | 3/2010 | Cindrich et al. |
| 7,682,340 | B2 | 3/2010 | Funamura et al. |
| 7,691,090 | B2 | 4/2010 | Belley et al. |
| 7,695,458 | B2 | 4/2010 | Belley et al. |
| 7,806,869 | B2 | 10/2010 | Nilsson et al. |
| 7,938,806 | B2 | 5/2011 | Fisher et al. |
| 8,016,791 | B2 | 9/2011 | Sugiki et al. |
| 8,034,035 | B2 | 10/2011 | Weaver et al. |
| 8,048,033 | B2 | 11/2011 | Becker et al. |
| 8,048,039 | B2 | 11/2011 | Carlyon et al. |
| 8,062,261 | B2 | 11/2011 | Adams |
| 8,096,976 | B2 | 1/2012 | Sugiki et al. |
| 8,105,287 | B2 | 1/2012 | Fisher et al. |
| 8,109,909 | B2 | 2/2012 | Tanabe et al. |
| 8,142,446 | B2 | 3/2012 | Shan |
| 8,251,923 | B2 | 8/2012 | Carrez et al. |
| 8,267,897 | B2 | 9/2012 | Wells |
| 8,286,657 | B2 | 10/2012 | Belley et al. |
| 8,317,754 | B2 | 11/2012 | Leeflang et al. |
| 8,357,119 | B2 | 1/2013 | Stout et al. |
| 8,361,020 | B2 | 1/2013 | Stout |
| 8,361,038 | B2 | 1/2013 | Mckinnon et al. |
| 8,366,684 | B2 | 2/2013 | Harding |
| 8,377,011 | B2 | 2/2013 | Weaver et al. |
| 8,388,583 | B2 | 3/2013 | Stout et al. |
| 8,469,928 | B2 | 6/2013 | Stout et al. |
| 8,500,696 | B2 | 8/2013 | Kobayashi et al. |
| 8,512,293 | B2 | 8/2013 | Leeflang et al. |
| 8,574,203 | B2 | 11/2013 | Stout et al. |
| 8,585,651 | B2 | 11/2013 | Asai |
| 8,622,967 | B2 | 1/2014 | Davis et al. |
| 8,622,972 | B2 | 1/2014 | Nystrom et al. |
| 8,636,695 | B2 | 1/2014 | Cluff et al. |
| 8,641,675 | B2 | 2/2014 | Stout et al. |
| 8,652,104 | B2 | 2/2014 | Goral et al. |
| 8,690,833 | B2 | 4/2014 | Belson |
| 8,715,242 | B2 | 5/2014 | Helm |
| 8,740,859 | B2 | 6/2014 | Mckinnon et al. |
| 8,747,387 | B2 | 6/2014 | Belley et al. |
| 8,814,833 | B2 | 8/2014 | Farrell et al. |
| 8,864,715 | B2 | 10/2014 | Cluff et al. |
| 8,932,258 | B2 | 1/2015 | Blanchard et al. |
| 8,932,259 | B2 | 1/2015 | Stout et al. |
| 8,939,938 | B2 | 1/2015 | Funamura et al. |
| 8,951,230 | B2 | 2/2015 | Tanabe et al. |
| 8,998,852 | B2 | 4/2015 | Blanchard et al. |
| 9,017,288 | B1 | 4/2015 | Starnes |
| 9,052,025 | B2 | 6/2015 | Zinn et al. |
| 9,089,671 | B2 | 7/2015 | Stout et al. |
| 9,095,679 | B2 | 8/2015 | Nishimura et al. |
| 9,101,746 | B2 | 8/2015 | Stout et al. |
| 9,101,748 | B2 | 8/2015 | Harding et al. |
| 9,101,749 | B2 | 8/2015 | Nakagami et al. |
| 9,108,021 | B2 | 8/2015 | Hyer et al. |
| 9,114,241 | B2 | 8/2015 | Stout et al. |
| 9,126,012 | B2 | 9/2015 | Mckinnon et al. |
| 9,155,863 | B2 | 10/2015 | Isaacson et al. |
| 9,155,864 | B2 | 10/2015 | Stout et al. |
| 9,155,876 | B2 | 10/2015 | Sonderegger et al. |
| 9,192,752 | B2 | 11/2015 | Leeflang et al. |
| 9,220,882 | B2 | 12/2015 | Belley et al. |
| 9,227,047 | B2 | 1/2016 | Khalaj |
| 9,233,230 | B2 | 1/2016 | Puhasmã£gi et al. |
| 9,242,071 | B2 | 1/2016 | Morgan et al. |
| 9,242,072 | B2 | 1/2016 | Morgan et al. |
| RE45,896 | E | 2/2016 | Stout et al. |
| 9,259,554 | B2 | 2/2016 | Ma et al. |
| 9,272,088 | B2 | 3/2016 | Bornhoft |
| 9,327,095 | B2 | 5/2016 | Ma |
| 9,352,119 | B2 | 5/2016 | Burkholz et al. |
| 9,352,127 | B2 | 5/2016 | Yeh et al. |
| 9,358,364 | B2 | 6/2016 | Isaacson et al. |
| 9,381,320 | B2 | 7/2016 | Vincent et al. |
| 9,399,116 | B2 | 7/2016 | Goral et al. |
| 9,408,569 | B2 | 8/2016 | Andreae et al. |
| 9,486,162 | B2 | 11/2016 | Zhuang et al. |
| 9,522,254 | B2 | 12/2016 | Belson |
| 9,545,495 | B2 | 1/2017 | Goral et al. |
| 9,579,486 | B2 | 2/2017 | Burkholz et al. |
| 9,579,490 | B2 | 2/2017 | Ma et al. |
| 9,592,367 | B2 | 3/2017 | Harding et al. |
| 9,604,030 | B2 | 3/2017 | Leeflang et al. |
| 9,604,035 | B2 | 3/2017 | Keyser et al. |
| 9,616,201 | B2 | 4/2017 | Belson |
| 9,737,686 | B2 | 8/2017 | Trainer et al. |
| 9,750,920 | B2 | 9/2017 | Vincent et al. |
| 9,750,925 | B2 | 9/2017 | Ma et al. |
| 9,750,927 | B2 | 9/2017 | Ma |
| 9,750,928 | B2 | 9/2017 | Burkholz et al. |
| 9,757,540 | B2 | 9/2017 | Belson |
| 9,770,580 | B2 | 9/2017 | Burkholz et al. |
| 9,775,972 | B2 | 10/2017 | Christensen et al. |
| 9,788,943 | B2 | 10/2017 | Deshmukh et al. |
| 9,789,280 | B2 | 10/2017 | Ma |
| 9,895,525 | B2 | 2/2018 | Ma et al. |
| 9,919,136 | B2 | 3/2018 | Lim et al. |
| 9,931,101 | B2 | 4/2018 | Okubo et al. |
| 9,937,322 | B2 | 4/2018 | Drake et al. |
| 9,943,677 | B2 | 4/2018 | Gordon et al. |
| 9,950,139 | B2 | 4/2018 | Blanchard et al. |
| 9,974,938 | B2 | 5/2018 | Pepin et al. |
| 9,999,746 | B2 | 6/2018 | Lareau et al. |
| 9,999,761 | B2 | 6/2018 | Joseph et al. |
| 10,052,474 | B2 | 8/2018 | Keyser et al. |
| 10,080,867 | B2 | 9/2018 | Goral et al. |
| 10,086,171 | B2 | 10/2018 | Belson |
| 10,105,085 | B2 | 10/2018 | Andreae et al. |
| 10,118,017 | B2 | 11/2018 | Isaacson et al. |
| 10,118,023 | B2 | 11/2018 | Yeh et al. |
| 10,159,820 | B2 | 12/2018 | Hall et al. |
| 10,188,845 | B2 | 1/2019 | Fischer et al. |
| 10,238,852 | B2 | 3/2019 | Burkholz et al. |
| 10,238,853 | B2 | 3/2019 | Kume et al. |
| 10,265,506 | B2 | 4/2019 | Borowicz |
| 10,286,185 | B2 | 5/2019 | Tanabe et al. |
| 10,321,933 | B1 | 6/2019 | Ramee et al. |
| 10,328,239 | B2 | 6/2019 | Belson |
| 10,357,635 | B2 | 7/2019 | Korkuch et al. |
| 10,426,929 | B2 | 10/2019 | Burkholz et al. |
| 10,426,931 | B2 | 10/2019 | Blanchard et al. |
| 10,441,773 | B2 | 10/2019 | Ma et al. |
| 10,463,840 | B2 | 11/2019 | Hyer et al. |
| 10,463,846 | B2 | 11/2019 | Gordon et al. |
| 10,478,593 | B2 | 11/2019 | Jones et al. |
| 10,478,609 | B2 | 11/2019 | Harding et al. |
| 10,493,262 | B2 | 12/2019 | Tran et al. |
| 10,500,329 | B2 | 12/2019 | Weaver et al. |
| 10,500,376 | B2 | 12/2019 | Isaacson et al. |
| 10,507,281 | B2 | 12/2019 | Burkholz et al. |
| 10,512,755 | B2 | 12/2019 | Hu et al. |
| 10,525,236 | B2 | 1/2020 | Belson |
| 10,543,351 | B2 | 1/2020 | Ma et al. |
| 10,543,354 | B2 | 1/2020 | Bihlmaier et al. |
| 10,549,073 | B2 | 2/2020 | Burkholz et al. |
| 10,596,351 | B2 | 3/2020 | Liska |
| 10,617,859 | B2 | 4/2020 | Lorimer et al. |
| 10,668,266 | B2 | 6/2020 | Lin et al. |
| 10,675,440 | B2 | 6/2020 | Abitabilo et al. |
| 10,688,280 | B2 | 6/2020 | Blanchard et al. |
| 10,709,828 | B2 | 7/2020 | Toellner et al. |
| 10,729,881 | B2 | 8/2020 | Lareau et al. |
| 10,729,882 | B2 | 8/2020 | Morgan et al. |
| 10,737,085 | B2 | 8/2020 | Rieckmann et al. |
| 10,765,853 | B2 | 9/2020 | Neff et al. |
| 10,799,680 | B2 | 10/2020 | Belson |
| 10,835,729 | B2 | 11/2020 | Agrawal et al. |
| 10,850,069 | B2 | 12/2020 | Solomon |
| 10,850,070 | B2 | 12/2020 | Naing et al. |
| 10,869,993 | B2 | 12/2020 | Ma et al. |
| 10,898,223 | B2 | 1/2021 | Harding et al. |
| 10,905,858 | B2 | 2/2021 | Farrell et al. |
| 10,926,063 | B2 | 2/2021 | Cupelli et al. |
| 10,933,217 | B2 | 3/2021 | Blackman et al. |
| 10,994,101 | B2 | 5/2021 | Ma et al. |

(56) References Cited

U.S. PATENT DOCUMENTS 11,000,678 B2 5/2021 Hall
11,033,713 B2 6/2021 Leeflang et al.
11,033,718 B2 6/2021 Belson
11,116,936 B2 9/2021 Harding et al.
11,135,399 B2 10/2021 Isaacson et al.
11,135,406 B2 10/2021 Ribelin et al.
11,147,957 B2 10/2021 Burkholz et al.
11,191,938 B2 12/2021 Snow
11,202,886 B2 12/2021 Belson
11,207,495 B2 12/2021 Goral et al.
11,213,656 B2 1/2022 Garrison et al.
11,219,747 B2 1/2022 Breindel et al.
11,224,720 B2 1/2022 Brunetti et al.
11,229,730 B2 1/2022 Teo et al.
11,260,146 B2 3/2022 Busam et al.
11,291,802 B2 4/2022 Naidu et al.
11,291,803 B2 4/2022 Burkholz et al.
11,291,805 B2 4/2022 Ouchi et al.
11,324,919 B2 5/2022 Ma
11,324,922 B2 5/2022 Trainer et al.
11,324,926 B2 5/2022 Harding
11,324,927 B2 5/2022 Cheng
11,324,939 B2 5/2022 Solomon et al.
11,338,113 B2 5/2022 Isaacson et al.
11,357,962 B2 6/2022 Burkholz et al.
11,389,624 B2 7/2022 Cook
11,406,810 B2 8/2022 Harding et al.
11,413,432 B2 8/2022 Hyer et al.
11,420,025 B2 8/2022 Thirumoorthy et al.
11,420,034 B2 8/2022 Solomon et al.
11,433,226 B2 9/2022 Kume et al.
11,439,794 B2 9/2022 Ebner et al.
11,446,467 B2 9/2022 Breindel et al.
11,446,472 B2 9/2022 Kumar et al.
11,452,847 B1 9/2022 Cook
11,452,858 B2 9/2022 Keyser et al.
11,478,610 B2 10/2022 Vincent et al.
11,504,500 B2 11/2022 Naidu et al.
11,511,098 B2 11/2022 Agrawal et al.
11,524,152 B1 12/2022 Leeflang et al.
11,529,474 B2 12/2022 Nakagami et al.
11,534,581 B2 12/2022 Isaacson et al.
11,534,591 B2 12/2022 Hu et al.
2008/0108944 A1* 5/2008 Woehr ............. A61B 5/150389 604/164.08
2013/0274683 A1* 10/2013 Stout ................. A61M 39/0208 604/256
2015/0038910 A1* 2/2015 Harding ................ A61M 39/10 604/167.02
2015/0151088 A1 6/2015 Lim et al.
2018/0361119 A1 12/2018 Goral et al.
2018/0361120 A1 12/2018 Goral et al.
2019/0001031 A1 1/2019 Real et al.
2019/0160258 A1 5/2019 Kristen
2019/0167966 A1 6/2019 Burkholz et al.
2019/0388653 A1 12/2019 Breindel et al.
2020/0046946 A1 2/2020 Staley et al.
2020/0061279 A1 2/2020 Weaver et al.
2020/0078515 A1 3/2020 Burkholz et al.
2020/0078556 A1 3/2020 Hu et al.
2020/0094024 A1 3/2020 Teoh
2020/0094037 A1 3/2020 Tran et al.
2020/0101265 A1 4/2020 Burkholz et al.
2020/0121896 A1 4/2020 Baid
2020/0155809 A1 5/2020 Burkholz et al.
2020/0179613 A1 6/2020 Branson et al.
2020/0179646 A1 6/2020 Kinoshita et al.
2020/0254195 A1* 8/2020 Nakagami ......... A61M 39/0693
2020/0261702 A1 8/2020 Jewell et al.
2020/0297969 A1 9/2020 Abitabilo et al.
2020/0297989 A1 9/2020 Rieckmann et al.
2020/0316347 A1 10/2020 Belson
2020/0324088 A1 10/2020 Harding et al.
2020/0405275 A1 12/2020 Abitabilo et al.
2021/0023358 A1 1/2021 Agrawal et al.
2021/0031008 A1 2/2021 Woehr et al.
2021/0031009 A1 2/2021 Solomon
2021/0038868 A1 2/2021 Naing et al.
2021/0052879 A1 2/2021 Spataro
2021/0068731 A1 3/2021 Kumar
2021/0068732 A1 3/2021 Yan et al.
2021/0069476 A1 3/2021 Ma et al.
2021/0106356 A1 4/2021 Harding et al.
2021/0113824 A1 4/2021 Chng et al.
2021/0146110 A1 5/2021 Nelson et al.
2021/0154439 A1 5/2021 Blanchard et al.
2021/0220619 A1 7/2021 Farrell et al.
2021/0228781 A1 7/2021 Scherich et al.
2021/0236790 A1 8/2021 Kume et al.
2021/0283376 A1 9/2021 Yamamoto et al.
2021/0299425 A1 9/2021 Kume et al.
2021/0299429 A1 9/2021 Naidu
2021/0346653 A1 11/2021 Burkholz et al.
2021/0361911 A1 11/2021 Isaacson et al.
2021/0370020 A1 12/2021 Gupta
2021/0379337 A1 12/2021 Yamamoto et al.
2021/0393918 A1 12/2021 Rasmussen et al.
2021/0393920 A1 12/2021 Yamamoto et al.
2021/0402143 A1 12/2021 Yokota et al.
2022/0001161 A1 1/2022 Burkholz et al.
2022/0023592 A1 1/2022 Scherich et al.
2022/0080159 A1 3/2022 Garrison et al.
2022/0088360 A1 3/2022 Snow
2022/0111191 A1 4/2022 Ma
2022/0152359 A1 5/2022 Naidu
2022/0161003 A1 5/2022 Cook
2022/0168548 A1 6/2022 Dong
2022/0176080 A1 6/2022 Ng et al.
2022/0225914 A1 7/2022 Chen et al.
2022/0226631 A1 7/2022 Natesan
2022/0233813 A1 7/2022 Ma
2022/0233816 A1 7/2022 Muskatello et al.
2022/0233817 A1 7/2022 Trainer et al.
2022/0233822 A1 7/2022 Cheng
2022/0233823 A1 7/2022 Harding
2022/0265986 A1 8/2022 Burkholz et al.
2022/0280757 A1 9/2022 Wada et al.
2022/0280767 A1 9/2022 Solomon et al.
2022/0296859 A1 9/2022 Sutton et al.
2022/0313959 A1 10/2022 Cook
2022/0322984 A1 10/2022 Millerd
2022/0339420 A1 10/2022 Harding et al.
2022/0355081 A1 11/2022 Thirumoorthy et al.
2022/0355093 A1 11/2022 Natesan et al.
2022/0362510 A1 11/2022 Lackey et al.
2022/0362516 A1 11/2022 Lackey et al.
2022/0362523 A1 11/2022 Huang et al.
2022/0370764 A1 11/2022 Ebner et al.
2022/0370765 A1 11/2022 Lackey et al.
2022/0379088 A1 12/2022 Scherich et al.
2022/0379103 A1 12/2022 Chen et al.
2022/0387762 A1 12/2022 Kumar et al.
2022/0401717 A1 12/2022 Bihlmaier et al.
2022/0409864 A1 12/2022 Kinoshita
2023/0012604 A1 1/2023 Vincent et al.

FOREIGN PATENT DOCUMENTS

EP 2 398 545 A1 12/2011
EP 2 593 166 A1 5/2013
EP 2 638 926 A1 9/2013
EP 2 763 740 A1 8/2014
EP 3 082 933 A1 10/2016
EP 3 266 490 A1 1/2018
EP 3 283 155 A1 2/2018
EP 3 337 549 A1 6/2018
EP 3 381 495 A1 10/2018
EP 3 466 479 A1 4/2019
EP 3 470 106 A1 4/2019
EP 3 509 513 A1 7/2019
EP 3 532 128 A1 9/2019
EP 3 552 652 A1 10/2019
EP 3 717 046 A1 10/2020
EP 3 893 984 A1 10/2021

(56) References Cited

FOREIGN PATENT DOCUMENTS

| | | | | | |
|---|---|---|---|---|---|
| EP | 3 911 395 | A2 | | 11/2021 | |
| EP | 3 967 344 | A1 | | 3/2022 | |
| JP | H03-167575 | A | | 7/1991 | |
| JP | H06-147186 | A | | 5/1994 | |
| JP | 3486188 | B2 | | 1/2004 | |
| JP | 4510619 | B2 | | 7/2010 | |
| JP | 4538471 | B2 | | 9/2010 | |
| JP | 5813765 | B2 | | 3/2011 | |
| JP | 4964592 | B2 | | 7/2012 | |
| JP | 4996015 | B2 | | 8/2012 | |
| JP | 5253534 | B2 | | 7/2013 | |
| JP | 5591833 | B2 | | 9/2014 | |
| JP | 2014-528808 | A | | 10/2014 | |
| JP | 2014-5288807 | A | | 10/2014 | |
| JP | 5603406 | B2 | | 10/2014 | |
| JP | 5813764 | B2 | | 11/2015 | |
| JP | 2016-526469 | A | | 9/2016 | |
| JP | 2016-527027 | A | | 9/2016 | |
| JP | 5997900 | B2 | | 9/2016 | |
| JP | 2017-006726 | A | | 1/2017 | |
| JP | 2018-511439 | A | | 4/2018 | |
| JP | 2019-162452 | | | 9/2019 | |
| JP | 6752814 | B2 | | 9/2020 | |
| WO | WO-2008052791 | A1 | * | 5/2008 | ........... A61B 5/1411 |
| WO | WO-2016/077234 | A1 | | 5/2016 | |
| WO | WO-2016/163939 | A1 | | 10/2016 | |
| WO | WO-2017/009483 | A1 | | 1/2017 | |
| WO | WO-2017/042825 | A2 | | 3/2017 | |
| WO | WO-2017/044029 | A1 | | 3/2017 | |
| WO | WO-2017/081226 | A1 | | 5/2017 | |
| WO | WO-2017/106673 | A2 | | 6/2017 | |
| WO | WO-2022/029190 | A1 | | 2/2022 | |
| WO | WO-2022/118837 | A1 | | 6/2022 | |
| WO | WO-2022/220331 | A1 | | 10/2022 | |
| WO | WO-2022/220332 | A1 | | 10/2022 | |
| WO | WO-2022/240594 | A1 | | 11/2022 | |
| WO | WO-2022/241189 | A1 | | 11/2022 | |
| WO | WO-2022/241193 | A1 | | 11/2022 | |
| WO | WO-2022/245703 | A1 | | 11/2022 | |
| WO | WO-2022/250931 | A1 | | 12/2022 | |
| WO | WO-2022/251015 | A1 | | 12/2022 | |

OTHER PUBLICATIONS

International Searching Authority, "International Search Report," issued in connection with International Patent Application No. PCT/JP2020/010601, dated Apr. 28, 2020.

International Searching Authority, "Written Opinion," issued in connection with International Patent Application No. PCT/JP2020/010601, dated Apr. 28, 2020.

Written Opinion of the International Search Authority, dated Apr. 28, 2020, issued in corresponding International Application No. PCT/JP2020/010601 (11 pages).

* cited by examiner

CATHETER ASSEMBLY

CROSS-REFERENCE TO RELATED APPLICATIONS

This application is a bypass continuation of PCT Application No. PCT/JP2020/010601, filed on Mar. 11, 2020, which claims priority to Japanese Application No. 2019-063152, filed on Mar. 28, 2019. The contents of these applications are hereby incorporated by reference in their entireties.

BACKGROUND

The present disclosure relates to, for example, a catheter assembly used in a case of performing an infusion, a blood transfusion, or the like.

In a case of constructing an introduction portion of an infusion or a blood transfusion for a patient, for example, a catheter assembly as disclosed in JP 2018-511439 A is used. This catheter assembly has a catheter (flexible catheter tube), a catheter hub fixed to the catheter, and an inner needle (hollow introducer needle) arranged within the catheter.

When using the catheter assembly, a user inserts the catheter and the inner needle into a patient's body. Then, the inner needle is pulled out from the catheter and the catheter hub. Thereafter, the user inserts various medical instruments into the catheter hub from which the inner needle has been pulled out, connects a connector of an infusion tube, and the like, thereby using the catheter assembly as the introduction portion.

Further, the catheter assembly disclosed in JP 2018-511439 A includes a valve body (elastic septum) that is provided in the catheter hub and can be opened and closed and an opening member (valve actuator) arranged on a proximal side of the valve. The valve body inhibits leakage of blood by blocking a space inside the catheter hub at the time of detaching the inner needle. The opening member penetrates through (opens) the valve body along with the insertion of the medical instrument, thereby enabling a medicinal liquid and blood to flow from a medical device side to the catheter side.

SUMMARY

Meanwhile, in the configuration in which the opening member penetrates through the valve body along with the introduction of the medical device as described above, there is a possibility that the opening member moves to open the valve body, for example, when an impact force is applied due to a fall or the like.

Therefore, one aspect of the present invention aims to provide a catheter assembly capable of inhibiting opening of a valve body due to movement of an opening member with a simple device configuration.

According to one embodiment, a catheter assembly includes: an inner needle with which a living body is punctured; a catheter through which the inner needle is inserted; a catheter hub provided at a proximal end of the catheter; a valve body provided in an internal space of the catheter hub; an opening member that has a cylindrical barrel portion, a neck portion extending from a distal end of the barrel portion while being reduced in diameter, and a foot portion extending to a proximal side of the barrel portion, is arranged on a proximal side of the valve body, and moves to a distal side along the internal space of the catheter hub to open the valve body by the neck portion; and a movement inhibiting mechanism that generates a resistance force against the movement of the opening member to the distal side. The movement inhibiting mechanism includes a contact portion that generates a frictional force against the catheter hub or the valve body.

According to the catheter assembly of the above embodiment, the opening of the valve body due to the movement of the opening member can be inhibited with a simple device configuration.

DETAILED DESCRIPTION

Hereinafter, embodiments of the present invention will be described in detail with reference to the accompanying drawings.

First Embodiment

Figure 1:
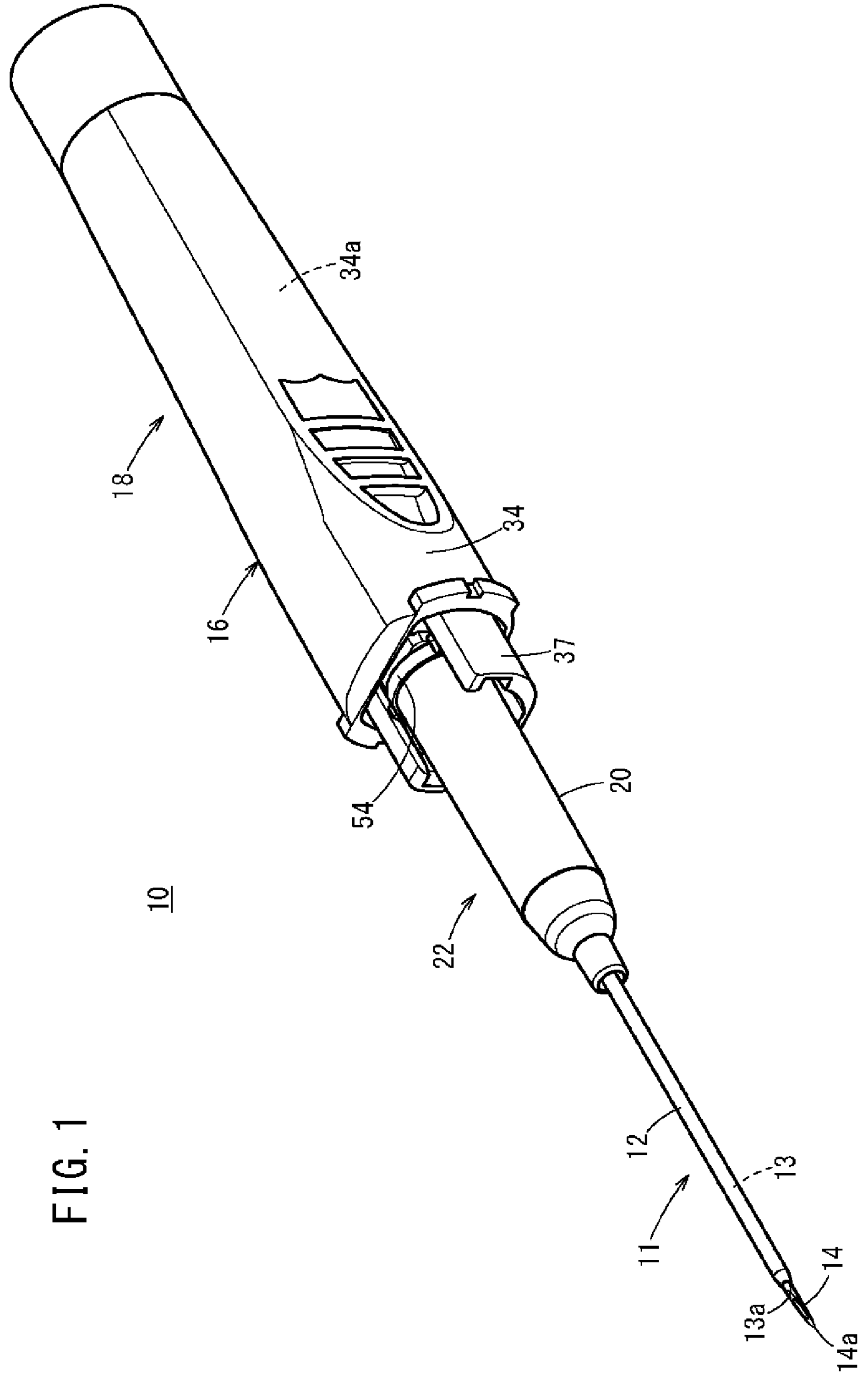
FIG. 1 is a perspective view of a catheter assembly according to a first embodiment.

A catheter assembly 10 according to the present embodiment has a catheter 12 that is inserted to indwell inside a patient's body (living body) as illustrated in FIG. 1, and is used to construct an inlet/outlet for a liquid (a medicinal liquid and blood) during an infusion, a blood transfusion, or the like. The catheter 12 is configured, for example, as a peripheral venous catheter. Incidentally, the catheter 12 may be a catheter longer than the peripheral venous catheter (for example, a central venous catheter, a PICC, a mid-line catheter, and the like). In addition, the catheter 12 is not limited to a venous catheter, and may be configured as an arterial catheter such as a peripheral arterial catheter.

As illustrated in the drawing, the catheter assembly 10 has an operating member 18 formed of an inner needle 14 and a needle hub 16 fixed to a proximal end of the inner needle 14. Further, the catheter assembly 10 has a catheter indwelling body 22 formed of the above-described catheter 12 and a catheter hub 20 fixed to a proximal end of the catheter 12.

The catheter assembly 10 is assembled with the operating member 18 from the proximal side of the catheter indwelling body 22 in an initial state (product provided state) before use, thereby forming a multi-structure needle 11 through which the inner needle 14 is inserted in the catheter 12. In the multi-structure needle 11, the needle tip 14*a* of the inner needle 14 protrudes, and the inner needle 14 and the catheter 12 can be integrally punctured the living body. Further, a valve body 24, an opening member 26, and a fixing member 28 are housed inside the catheter hub 20 as illustrated in FIG. 2.

When using the catheter assembly 10 illustrated in FIG. 1, a user, such as a doctor and a nurse, grips and operates the needle hub 16 in the initial state to puncture the multi-structure needle 11 into the patient's body, thereby setting a puncture state in which the needle tip 14*a* reaches a blood vessel. Further, the user inserts the catheter 12 into the blood vessel by advancing the catheter 12 relative to the inner needle 14 while maintaining the puncture state. Thereafter, the user removes the inner needle 14 from the catheter 12 such that the catheter 12 indwells in the blood vessel. A connector 95 (see FIG. 4B) or the like is connected to the catheter 12 indwelling in the blood vessel via the catheter hub 20. Through this connector 95, treatment such as administration of a medicinal liquid or blood and blood sampling is performed. Hereinafter, each configuration of the catheter assembly 10 will be further described.

Figure 2:
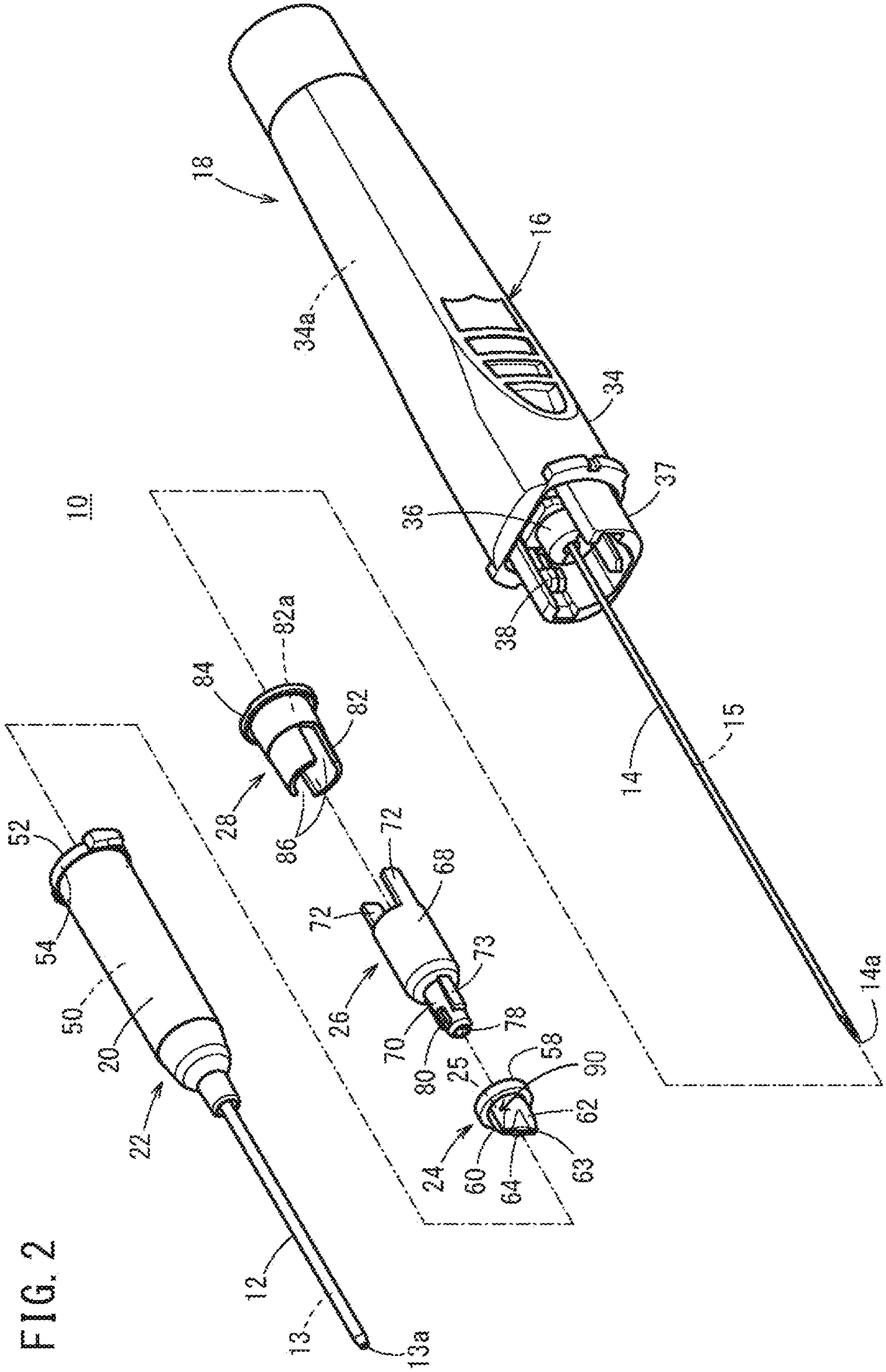
FIG. 2 is an exploded perspective view of the catheter assembly of FIG. 1.

As illustrated in FIG. 2, the inner needle 14 of the catheter assembly 10 (the operating member 18) is configured as a hollow tube having rigidity capable of puncturing a skin of a living body, and has the sharp needle tip 14*a* at a distal end thereof. Inside the inner needle 14, a hollow portion 15 is provided along the axial direction. The needle tip 14*a* is formed at a distal end of a blade surface inclined at a predetermined angle with respect to the axial direction of the inner needle 14. A groove or a hole communicating with the hollow portion 15 for flashback that guides blood to the proximal side at the time of puncturing a blood vessel may be formed on an outer peripheral surface of the inner needle 14.

Examples of a constituent material of the inner needle 14 include a metal material such as stainless steel, aluminum or an aluminum alloy, and titanium or a titanium alloy, a hard resin, ceramics, and the like. The inner needle 14 is firmly fixed to the needle hub 16 by a fixing means such as fusion, adhesion, and fitting.

The needle hub 16 forms a grip portion to be gripped by the user in the initial state in which the catheter indwelling body 22 and the operating member 18 are assembled. The needle hub 16 includes a hub main body 34 that is directly gripped by the user, and an inner needle support portion 36 that is integrally molded at a distal end of the hub main body 34.

The hub main body 34 is formed to have a shape and a size that allow the multi-structure needle 11 to be stably operated. The hub main body 34 is formed in a cylindrical shape on the proximal side and is gradually deformed into an elliptical shape toward the distal side, and has a cavity portion 34*a* formed inside.

The inner needle support portion 36 is formed in a columnar shape protruding from the hub main body 34 in the distal direction, and holds a proximal portion of the inner needle 14 at the central portion thereof. A pair of arms 38 to hold a flange 54 of the catheter hub 20 are provided on both side portions of the inner needle support portion 36. The arm 38 is housed in an arm accommodating portion 37 that restricts the outward displacement of the arm 38. The arm accommodating portion 37 is assembled so as to be capable of moving backward with respect to the arm 38, and is configured such that a distal end of the arm 38 is open outward to release the engagement with the catheter hub 20 when the arm accommodating portion 37 retracts from the arm 38.

A constituent material of the needle hub 16 is not particularly limited, but a thermoplastic resin, such as polypropylene, polycarbonate, polyamide, polysulfone, polyarylate, and a methacrylate-butylene-styrene copolymer can be applied.

On the other hand, the catheter 12 is formed as a flexible hollow body in which a lumen 13 is formed inside. An outer shape of the catheter 12 and the lumen 13 are formed in a perfect circular shape in cross-sectional view orthogonal to the axial direction, and extend along the axial direction of the catheter 12. The lumen 13 communicates with a distal opening 13*a* formed at a distal end of the catheter 12 and a proximal opening 13*b* (see FIG. 4A) formed at a proximal end of the catheter 12.

A material forming the catheter 12 is not particularly limited, but a transparent soft resin material may be applied. For example, a fluorine-based resin such as polytetrafluoroethylene (PTFE), an ethylene-tetrafluoroethylene copolymer (ETFE), and a perfluoroalkoxy fluorine resin (PFA), an olefin-based resin such as polyethylene and polypropylene or a mixture thereof, polyurethane, polyester, polyamide, a polyether nylon resin, a mixture of the olefin-based resin and an ethylene-vinyl acetate copolymer, and the like may be used.

A length of the catheter 12 is not particularly limited, and can be appropriately designed according to the application, various conditions, and the like, and is set to, for example, about 14 to 500 mm. The proximal end of the catheter 12 is inserted and fixed inside the catheter hub 20.

The catheter hub 20 is arranged on a patient's skin in a state in which the catheter 12 has been inserted into the patient's blood vessel, and is fixed onto the skin with a tape or the like, thereby being placed together with the catheter 12. A material forming the catheter hub 20 is not particularly limited, but, for example, the materials used for the needle hub 16 can be appropriately adopted.

The catheter hub 20 is formed in a tubular shape tapered in a distal direction. An internal space 50 is provided inside the catheter hub 20, and the internal space 50 communicates with the proximal opening 13*b* (see FIG. 4A) of the lumen 13 of the catheter 12 on the distal side. Further, the proximal side of the internal space 50 communicates with a proximal opening portion 52 of the catheter hub 20. The valve body 24, the opening member 26, and the fixing member 28 are housed in the internal space 50. Further, the flange 54 extending along the circumferential direction is provided on an outer peripheral surface of the catheter hub 20 on the proximal side.

The catheter 12 and the catheter hub 20 are fixed by a fixing means such as caulking, fusion, adhesion, and fitting. Incidentally, a caulking pin 56 is inserted, and the catheter 12 is sandwiched between the inner wall 20*a* of the catheter hub 20 and the caulking pin 56 to fix the catheter 12 in the example of FIG. 4A.

As illustrated in FIG. 2, the valve body 24 is arranged in the internal space 50 of the catheter hub 20, and forms a hemostatic valve that inhibits blood, which flows from the lumen 13 of the catheter 12 into the internal space 50, from leaking to the proximal opening portion 52. Although not particularly limited, the valve body 24 can be configured as a duckbill valve. Further, the valve body 24 may be a disc valve.

Figures 4A, 4B:
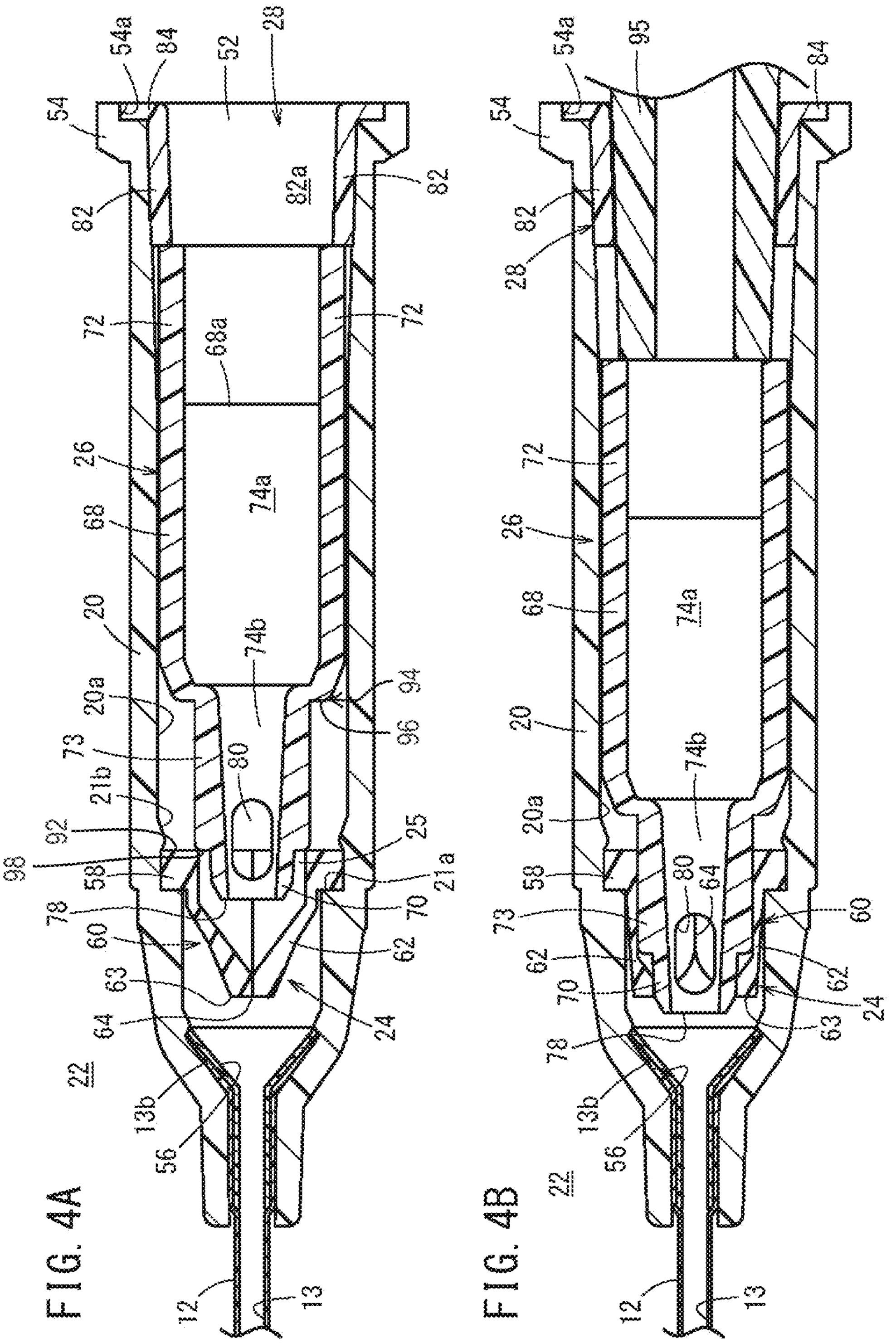
FIG. 4A is a cross-sectional view illustrating a state in which the opening member is attached to a catheter hub of FIG. 1.
FIG. 4B is a cross-sectional view illustrating a state in which a valve body of the catheter hub of FIG. 4A is opened.

For example, the valve body 24 has an annular portion 58 fixed to the inner wall 20*a* of the catheter hub 20 and a valve main body 60 protruding from the annular portion 58 in the distal direction. As illustrated in FIG. 4A, the inner wall 20*a* of the catheter hub 20 is provided with a stepped portion 21*a* protruding inward and a locking convex portion 21*b* provided to be apart on the proximal side of the stepped portion 21*a* in order to attach the valve body 24. The valve body 24 is immovably fixed as the annular portion 58 is sandwiched between the stepped portion 21*a* and the locking convex portion 21*b*.

The valve main body 60 is formed in a cylindrical shape on the annular portion 58 side and is formed in a tubular shape having a pair of inclined portions 62 that approach each other in the distal direction. A valve space 25 that narrows in the distal direction is formed inside the valve body 24.

Further, an end surface 63 extending in the width direction is formed at distal ends of the pair of inclined portions 62. A slit 64 is formed in the end surface 63. The slit 64 extends along the longitudinal direction of the end surface 63, extends between the pair of inclined portions 62 to a side portion 90 of the valve main body 60, and extends to a distal end of the annular portion 58. The slit 64 allows the insertion of the inner needle 14 and is restored by an elastic restoring force after the inner needle 14 is removed.

Further, the pair of inclined portions 62 of the valve main body 60 are configured to be greatly separated from each other to open the slit 64 as illustrated in FIG. 4B along with the insertion of the opening member 26 arranged on the proximal side. As a result, a force with which the opening member 26 inserts the valve body 24 can be reduced. Further, since the valve body 24 includes the pair of inclined portions 62 and the slit 64, a force of pushing the opening member 26 back to the proximal side is weakened, so that it is easy to maintain an open state of the valve body 24 achieved by the opening member 26.

Figure 3:
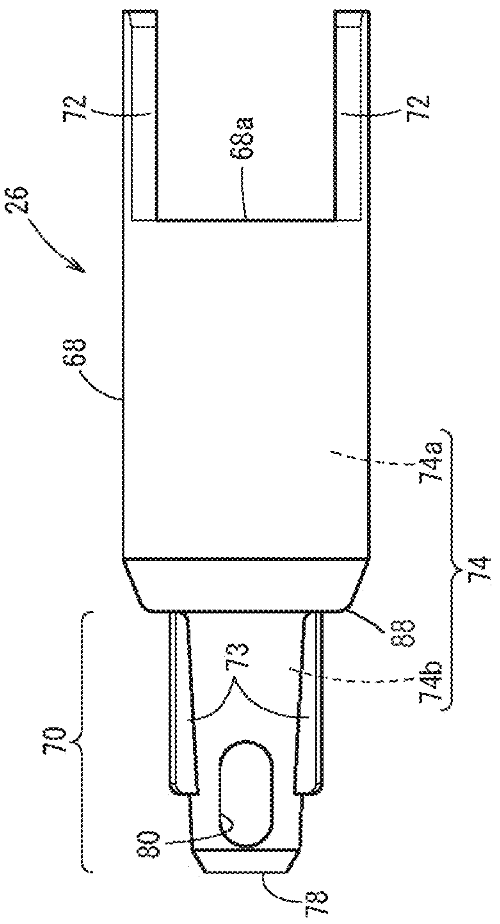
FIG. 3 is a side view of an opening member of FIG. 1.

As illustrated in FIG. 3, the opening member 26 includes a cylindrical barrel portion 68, a neck portion 70 that is connected to a distal end of the barrel portion 68, has a smaller diameter than the barrel portion 68, and protrudes in the distal direction, and a pair of foot portions 72 that are connected to a proximal end of the barrel portion 68 and protrude in the proximal direction. As illustrated in FIG. 4A, a space portion 74 is formed inside the barrel portion 68 and the neck portion 70.

The barrel portion 68 is formed to have an outer diameter slightly smaller than an inner diameter of the internal space 50 of the catheter hub 20, and includes a barrel-portion-side space portion 74*a* that is a part of the space portion 74 inside. An outer peripheral surface of the barrel portion 68 is formed in a circular shape in cross-sectional view orthogonal to the axial direction of the opening member 26. The barrel-portion-side space portion 74*a* communicates with a proximal opening 68*a* provided at a proximal end of the barrel portion 68.

The neck portion 70 is formed to have a diameter that can be inserted inside the annular portion 58 of the valve body 24. As illustrated in FIG. 4B, the neck portion 70 is configured to penetrate through the slit 64 of the valve body 24 to push and widen the pair of inclined portions 62 and widely open the valve main body 60 when the opening member 26 moves in the distal direction. The neck portion 70 has a width that allows insertion with respect to a proximal-portion-side inlet of the valve space 25, but a shoulder portion 94, which is a step between the barrel portion 68 and the neck portion 70, is wider than the proximal-portion-side inlet of the valve space 25 so that a distal surface 96 of the shoulder portion 94 abuts on the annular portion 58. Therefore, the movement of the opening member 26 to the distal side of such an abutment position is restricted. Therefore, a favorable positional relationship that suppresses blood retention between the pair of side holes 80 provided in the neck portion 70 and the slit 64 of the valve body 24 can be maintained. Incidentally, the shoulder portion 94 has a shape that does not come into contact with the locking convex portion 21*b*, for example, a shape in which an end surface of the shoulder portion 94 is chamfered.

As illustrated in FIG. 3, a rib structure is formed on an outer peripheral portion of the neck portion 70 so as to protrude radially outward. The rib structure is formed of a pair of neck ribs 73 (a movement inhibiting mechanism as a contact portion). Incidentally, the neck ribs 73 are not limited to the pair, and one or a plurality of neck ribs 73 may be arranged, but a case where the pair of neck ribs 73 are provided will be described here as an example. The pair of neck ribs 73 are arranged so as to oppose each other while being separated by 180° in the circumferential direction. The neck rib 73 is formed to have a predetermined length along the axial direction from a boundary portion 88 between the barrel portion 68 and the neck portion 70 to the middle of the axially distal side of the neck portion 70. As illustrated in FIG. 4A, a distal end surface 98 of the neck rib 73 is formed so as to project outward from an inner diameter of the annular portion 58, and the neck rib 73 is configured to abut on a proximal portion (proximal end surface 92) of the annular portion 58. The neck rib 73 is configured to restrict the movement of the opening member 26 in the distal direction by being caught by the annular portion 58 when an impact load due to a fall or the like acts on the opening member 26. The rib structure can also be called a restriction means for restricting the movement of the opening member 26 in the distal direction.

An axial length of the neck rib 73 is set such that a distal end of the neck portion 70 is separated from the valve main body 60 when the neck rib 73 abuts on the proximal portion of the annular portion 58. Incidentally, the neck rib 73 is formed in a size that enters an inner diameter portion of the annular portion 58 and does not interfere with the movement of the opening member 26 in the distal direction when the opening member 26 is pressed to the distal side with a force equal to or greater than a predetermined load.

The opening member 26 is arranged proximal of the valve main body 60 of the valve body 24 in an initial state. In this state, the neck portion 70 at the distal end of the opening member 26 is configured to be maintained in the state of being separated from the valve main body 60 and to inhibit the opening of the valve body 24.

As illustrated in FIG. 4A, a neck-portion-side space 74*b*, which is a part of the space portion 74, is formed inside the neck portion 70. The neck-portion-side space 74*b* extends along the axial direction of the neck portion 70 and has a distal end communicating with a distal opening 78 formed at the distal end of the neck portion 70 and a proximal end communicating with the barrel-portion-side space portion 74*a*. Further, the distal side of the neck portion 70 is formed in a tapered shape whose diameter gradually decreases in the distal direction of the opening member 26.

The pair of side holes 80 are formed in the tapered portion of the distal end of the neck portion 70. The pair of side holes 80 oppose each other with the neck-portion-side space 74*b* interposed therebetween. Each of the side holes 80 is provided at a predetermined distance from the distal opening 78, penetrates the neck portion 70 in the thickness direction, and causes the neck-portion-side space 74*b* to communicate with the outside of the neck portion 70.

The opening member 26 is positioned such that the slit 64 of the valve body 24 and the pair of side holes 80 are at the same phase (circumferential position) in the initial state. With such positioning, each of the side holes 80 is exposed to a site where the slit 64 of the valve body 24 is open when the opening member 26 opens the valve main body 60 along with the insertion of the connector 95 as illustrated in FIG. 4B. That is, the pair of side holes 80 are located distal of a part of the slit 64 on the most proximal side in the state in which the opening member 26 opens the valve body 24.

When the neck rib 73 of the opening member 26 abuts on the proximal portion of the annular portion 58, the distal opening 78 of the opening member 26 is positioned so as not to come into contact with inner surfaces of the pair of inclined portions 62 of the valve main body 60. That is, the distal opening 78 of the opening member 26 is located proximal of the inner surface portion of the inclined portion 62 located on a path where the distal opening 78 of the opening member 26 moves to the distal side. As a result, it is possible to inhibit the opening member 26 from inadvertently opening the valve main body 60 before use.

As illustrated in FIG. 3, the pair of foot portions 72 are provided on the proximal side of the barrel portion 68 so as to oppose each other. The foot portion 72 is formed as a rectangular piece having a predetermined length in the proximal direction. Each of the foot portions 72 is formed in an arc shape according to an outer diameter shape of the barrel portion 68 when viewed from the axially proximal side. As illustrated in FIG. 4B, a proximal end of the foot portion 72 protrudes inward from an inner peripheral surface of the fixing member 28. When the connector 95 is inserted into the catheter hub 20, a distal portion of the connector 95 comes into contact with the proximal end of the foot portion 72. Therefore, the opening member 26 moves in the distal direction under a pressing force of the connector 95.

As illustrated in FIG. 2, the fixing member 28 is an inner member that inhibits detachment of the opening member 26 arranged in the internal space 50 of the catheter hub 20. The fixing member 28 performs a function of restricting the rotation of the opening member 26 in the circumferential direction with respect to the catheter hub 20. The fixing member 28 is fixed to the catheter hub 20 by fitting the opening member 26 into the inner wall 20*a* of the catheter hub 20 in a state of being housed in the internal space 50. Incidentally, a fixing means between the catheter hub 20 and the fixing member 28 is not particularly limited, and may be fitting, adhesion, fusion, or the like.

The fixing member 28 includes a fixed tubular body 82 having a through-hole 82*a*, and an annular convex portion 84 provided at a proximal end of the fixed tubular body 82. The proximal end of the fixed tubular body 82 forms the proximal opening portion 52 of the catheter hub 20. The fixed tubular body 82 is formed with a pair of notch portions 86 in which the pair of foot portions 72 of the opening member 26 are inserted. The pair of notch portions 86 are provided at opposing positions with the through-hole 82*a* interposed therebetween, and extend in the proximal direction from a distal end of the fixed tubular body 82. The annular convex portion 84 is arranged in a tubular groove portion 54*a* inside the flange 54 formed at the proximal end of the catheter hub 20 to inhibit the displacement of the fixing member 28 in the distal direction as illustrated in FIG. 4A.

The catheter assembly 10 according to the present embodiment is configured as described above, and effects thereof will be described hereinafter.

The catheter assembly 10 is used in a case of constructing the inlet/outlet for the infusion, the blood transfusion, the blood sampling, or the like to the patient. The user grips and operates the needle hub 16 of the catheter assembly 10 in the initial state illustrated in FIG. 1 to puncture the patient with the multi-structure needle 11.

When the needle tip 14*a* of the inner needle 14 reaches the blood vessel, blood flows into the lumen 13 of the catheter 12. As a result, the user can visually recognize a flashback of blood and confirm that the lumen 13 has been inserted in the blood vessel. When flowing inside the lumen 13 of the catheter 12 in the proximal direction, the blood flows into the internal space 50 of the catheter hub 20 from the proximal opening 13*b* (see FIG. 4A). In the internal space 50, the valve body 24 is inserted through the inner needle 14, but seals the periphery of the inner needle 14, so that the outflow of blood to a site proximal of the valve body 24 can be suppressed.

In the puncture state, the user advances the catheter 12 relative to the inner needle 14 and inserts the catheter 12 into the blood vessel. At a stage where the catheter 12 is inserted into the blood vessel to some extent, the operating member 18 is retracted with respect to the catheter indwelling body 22. As a result, the inner needle 14 is detached from the catheter 12.

In the catheter hub 20, when the needle tip 14*a* of the inner needle 14 is pulled out from the valve body 24, the valve main body 60 is elastically restored, and the slit 64 is closed. As a result, blood is blocked by the valve body 24, and blood is inhibited from flowing out to the proximal side. Further, if the inner needle 14 and the needle hub 16 are retracted, the inner needle 14 is detached from the proximal opening 13*b* of the catheter hub 20. That is, the inside of the catheter hub 20 is in the state illustrated in FIG. 4A. The catheter indwelling body 22 in this state is set to indwell in the patient.

As illustrated in FIG. 4A, the opening member 26 is inhibited from moving toward the distal side in the indwelling state of the catheter indwelling body 22 as the neck rib 73 of the opening member 26 is caught by the annular portion 58. As a result, it is possible to inhibit unintentional opening of the valve body 24.

In the indwelling state of the catheter indwelling body 22, the user can insert the connector 95, which communicates with a tube of an infusion line, a syringe, or the like, into the internal space 50 through the proximal opening of the catheter hub 20 as illustrated in FIG. 4B. The connector 95 is inserted inside the fixing member 28. The proximal end of the foot portion 72 of the opening member 26 protrudes inward from the fixing member 28, and thus, comes into contact with a distal end of the connector 95. As a result, the user can push the opening member 26 in the distal direction at the time of connecting the connector 95. When the opening member 26 is pushed in, the pair of foot portions 72 are guided by the notch portions 86 (see FIG. 2) of the fixing member 28 to move, and thus, move forward without rotating in the circumferential direction.

As the opening member 26 is pressed via the connector 95, the neck rib 73 moves inside the valve body 24 while pushing and widening the annular portion 58. Then, the neck portion 70 opens the slit 64 by separating the pair of inclined portions 62 from each other as illustrated in FIG. 4B. In an insertion completion state in which the connector 95 is fitted to the catheter hub 20, the neck portion 70 of the opening member 26 greatly separates the pair of inclined portions 62. Then, the pair of side holes 80 of the neck portion 70 are arranged in a portion where the slit 64 of the valve body 24 is widely opened.

The catheter assembly 10 of the present embodiment has the following effects.

The catheter assembly 10 of the present embodiment includes: the inner needle 14 with which the living body is punctured; the catheter 12 through which the inner needle 14 is inserted; the catheter hub 20 provided at the proximal end of the catheter 12; the valve body 24 provided in the internal space 50 of the catheter hub 20; and the opening member 26 that has the cylindrical barrel portion 68, the neck portion 70 extending from the distal end of the barrel portion 68 while being reduced in diameter, and the foot portion 72 extending to the proximal side of the barrel portion 68, is arranged on the proximal side of the valve body 24, and moves to the distal side along the internal space 50 of the catheter hub 20 to open the valve body 24 by the neck portion 70; and the movement inhibiting mechanism that generates the resistance force against the movement of the opening member 26 to the distal side. The movement inhibiting mechanism includes the contact portion that generates the frictional force against the catheter hub 20 or the valve body 24.

According to the catheter assembly 10, the contact portion can inhibit the opening member 26 from moving to the distal side due to an impact or the like, and thus, the valve body 24 can be inhibited from being opened unintentionally.

In the above-described catheter assembly 10, the contact portion may include the neck rib 73 that protrudes toward the outer peripheral side of the neck portion 70 and abuts on the valve body 24. With this configuration, the neck rib 73 restricts the movement of the opening member 26 to the distal end, so that the valve body 24 can be inhibited from being open unintentionally. Further, regarding details of the neck rib 73, for example, both sides of a rib width can be reduced in diameter in a tapered shape toward the outer periphery to appropriately adjust a frictional force and push the opening member 26 in the distal direction. Further, corners of the contact portion and the side surface are preferably rounded.

The opening member 26 has been described with the embodiment in which the cylindrical barrel portion 68, the neck portion 70 extending from the distal end of the barrel portion 68 while being reduced in diameter, and the foot portion 72 extending to the proximal side of the barrel portion 68, but may adopt a mode of being formed of the cylindrical barrel portion 68 and the neck portion 70 extending from the distal end of the barrel portion 68. Even in such a mode, the above-described effects can be achieved by providing a movement inhibiting mechanism that generates a resistance force against the movement of the opening member 26 to the distal side and providing the movement inhibiting mechanism with a contact portion that generates a frictional force against the catheter hub 20 or the valve body 24.

Hereinafter, other embodiments of the present invention will be described. Incidentally, an element having the same configuration or the same function as that of the first embodiment will be denoted by the same reference sign, and the detailed description thereof will be omitted in the following description.

Second Embodiment

Figure 5:
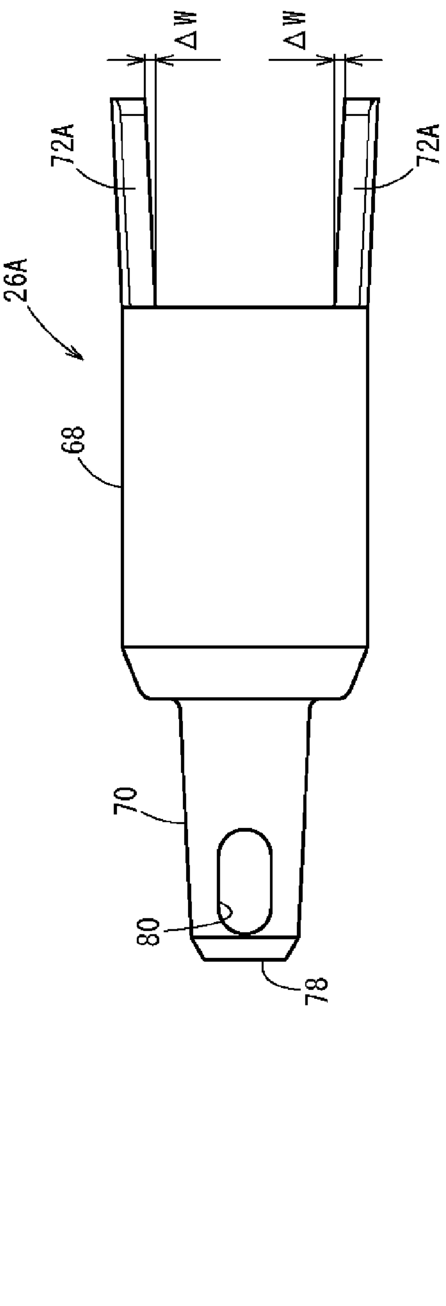
FIG. 5 is a side view of an opening member according to a second embodiment.

As illustrated in FIG. 5, an opening member 26A according to a second embodiment is not provided with the neck rib 73 (see FIG. 3) on the neck portion 70. Instead, a pair of foot portion 72A are formed to gradually widen outward to the proximal side. The foot portion 72A is formed so as to be inclined to be widen outward by a width ΔW at a proximal portion. A distance between outer surfaces of the pair of foot portions 72A is larger than an inner diameter of the inner wall 20*a* of the catheter hub 20.

Figure 6A:
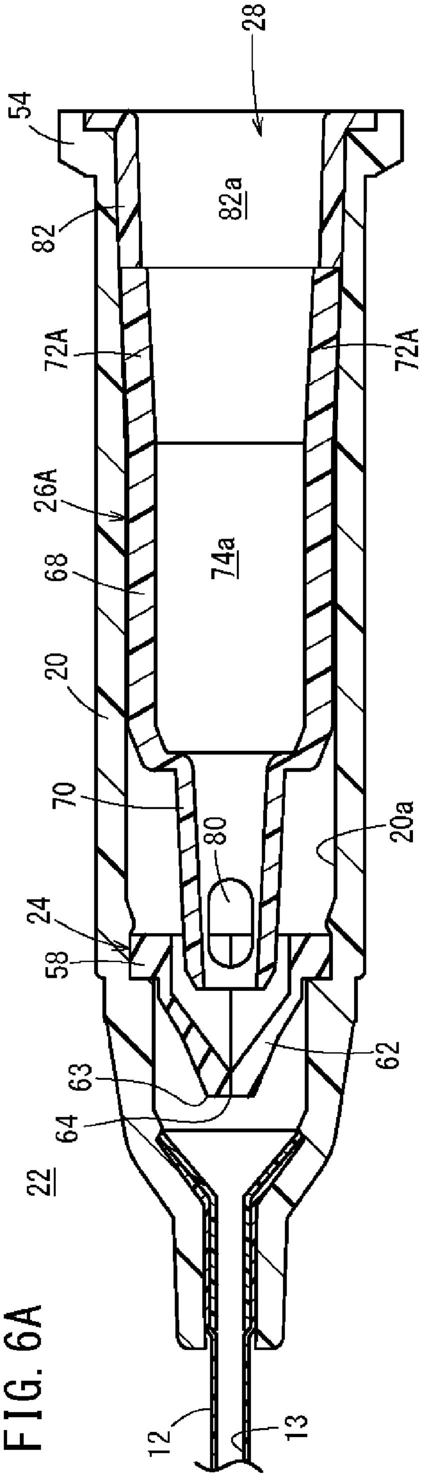
FIG. 6A is a cross-sectional view illustrating a state in which the opening member is inserted into a catheter hub according to the second embodiment.

As illustrated in FIG. 6A, when the opening member 26A is inserted into the internal space 50 of the catheter hub 20, the foot portion 72A is elastically deformed inward. At that time, the foot portion 72A exerts a frictional force by pressing and abutting on the inner wall 20*a* of the catheter hub 20 due to an elastic restoring force, and restricts the movement of the opening member 26A in the distal direction. That is, the foot portion 72A forms a movement inhibiting mechanism that generates a resistance force against the movement of the opening member 26A to the distal side in the present embodiment.

Figure 6B:
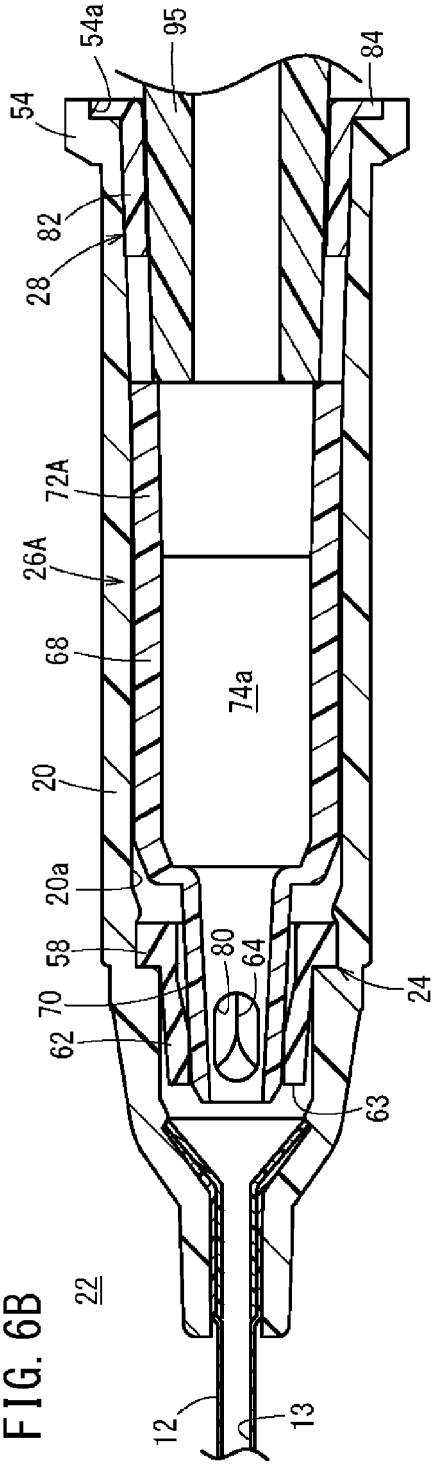
FIG. 6B is a cross-sectional view illustrating a state in which a valve body of the catheter hub of FIG. 6A is opened.

As illustrated in FIG. 6B, the opening member 26A of the present embodiment moves in the distal direction to open the valve body 24 along with the insertion of the connector 95. Incidentally, a frictional force generated on the outer surface of the foot portion 72A is appropriately set within a range that does not make it difficult to attach the connector 95 to the catheter hub 20. The frictional force generated on the outer surface of the foot portion 72A can be appropriately adjusted by the inclination of the foot portion 72A and the rigidity of the foot portion 72A.

First Modification of Second Embodiment

Figure 7A:
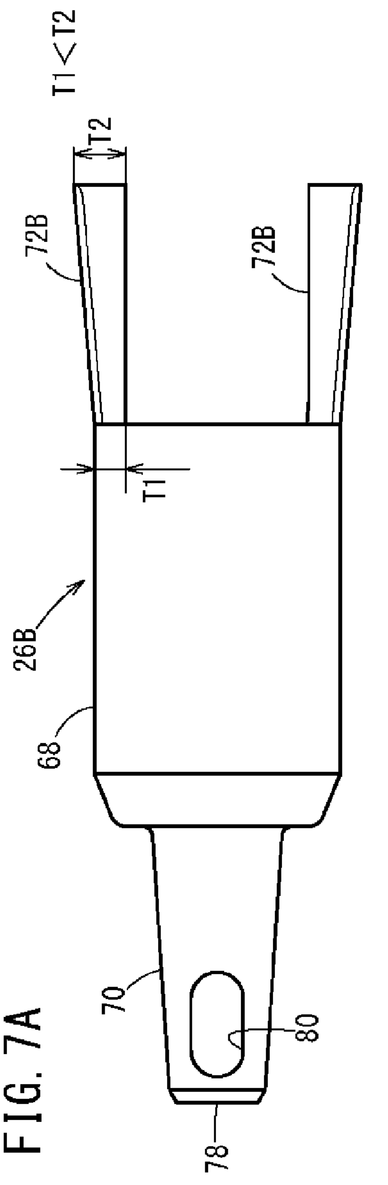
FIG. 7A is a side view of an opening member according to a first modification of the second embodiment.

As illustrated in FIG. 7A, an opening member 26B according to the present modification includes a foot portion 72B whose wall thickness increases toward a proximal portion. The foot portion 72B is formed such that a wall thickness T1 gradually increases to a wall thickness T2 from the distal side to the proximal side. An inner peripheral surface of the foot portion 72B extends in a direction parallel to the axial direction of the opening member 26B, and an outer peripheral surface of the foot portion 72B is formed so as to gradually widen outward toward the proximal portion.

According to the opening member 26B provided with such a foot portion 72B, it is possible to obtain the same effects as those of the opening member 26A formed with the foot portion 72A widening outward.

Second Modification of Second Embodiment

Figure 7B:
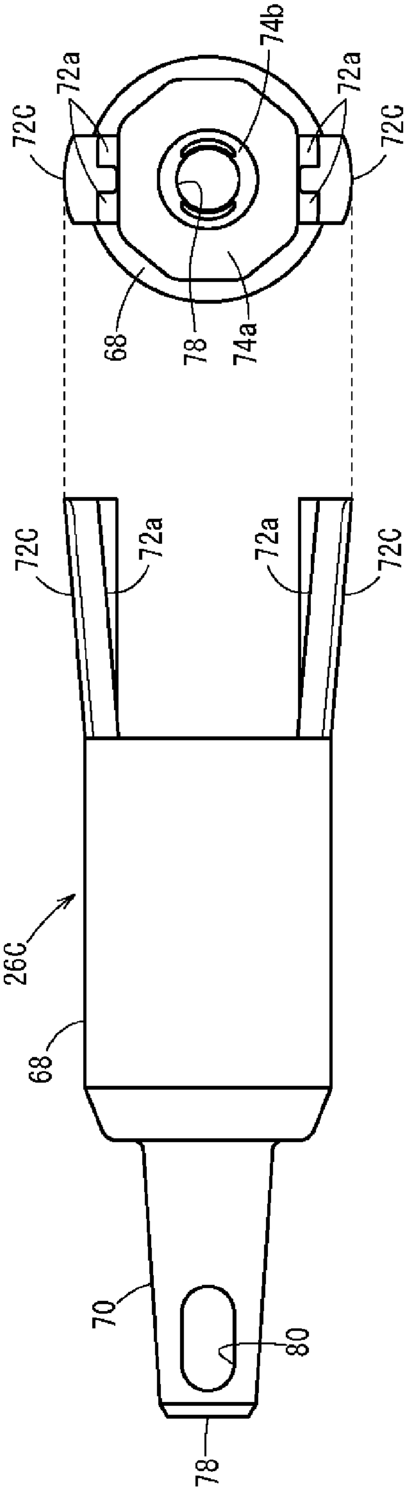
FIG. 7B is a view illustrating a side surface and a proximal end surface of an opening member according to a second modification of the second embodiment.

As illustrated in FIG. 7B, an opening member 26C according to the present modification includes a foot portion 72C whose wall thickness gradually increases toward the proximal side. The foot portion 72C of the opening member 26C of the present modification is similar to the foot portion 72B of the opening member 26B of FIG. 7A in terms of the wall thickness. However, a notch portion 72*a* is formed by cutting out a part of the foot portion 72C in a groove shape. As illustrated in the drawing, each of the foot portions 72C is formed with a pair of the notch portions 72*a* so as to form a T shape when viewed from the proximal side. With this configuration, the rigidity of the foot portion 72C can be adjusted within an appropriate range to adjust a frictional force.

Third Embodiment

Figure 8A:
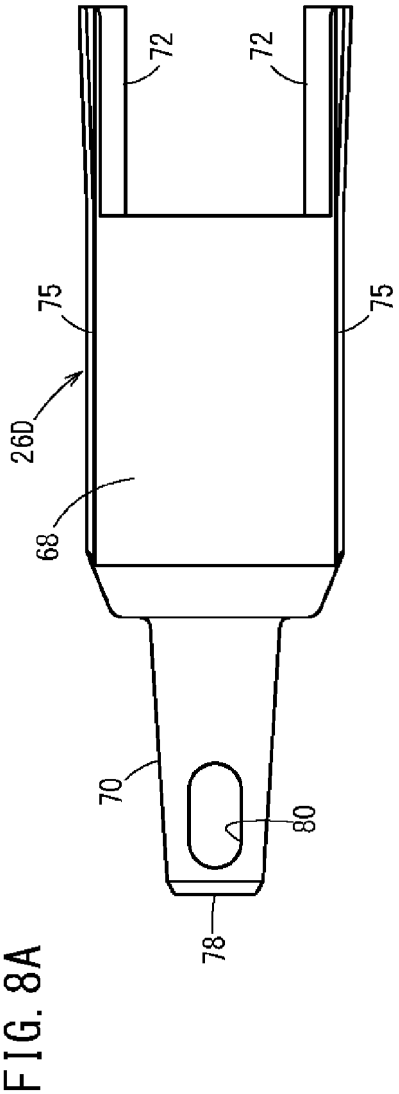
FIG. 8A is a side view of an opening member according to a third embodiment.
Figure 8B:
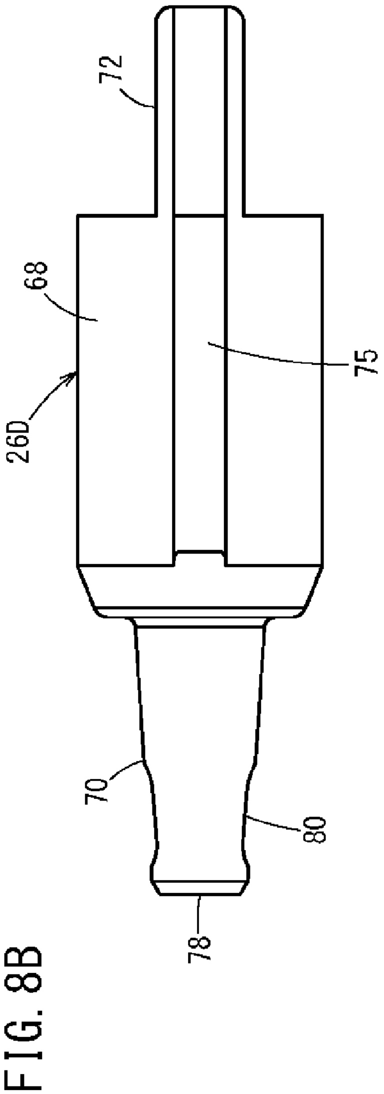
FIG. 8B is a plan view of the opening member of FIG. 8A.

As illustrated in FIG. 8A, an opening member 26D according to the present embodiment has a thin rib structure 75 (protruding structure) formed in a part from the outer circumference of the barrel portion 68 to the outer circumference of the foot portion 72. A pair of the rib structures 75 are provided to correspond to the foot portions 72. As illustrated in FIG. 8B, the rib structure 75 is formed so as to extend to be straight (linearly) in the axial direction from a proximal portion of the foot portion 72 to a vicinity of a distal end of the barrel portion 68. Further, the rib structure 75 may be provided only in the barrel portion 68.

Incidentally, the rib structure 75 has a structure in which the thickness of the foot portion 72 is gradually increased toward the proximal side, so that the same effects as those of the second embodiment can be obtained.

Figure 9:
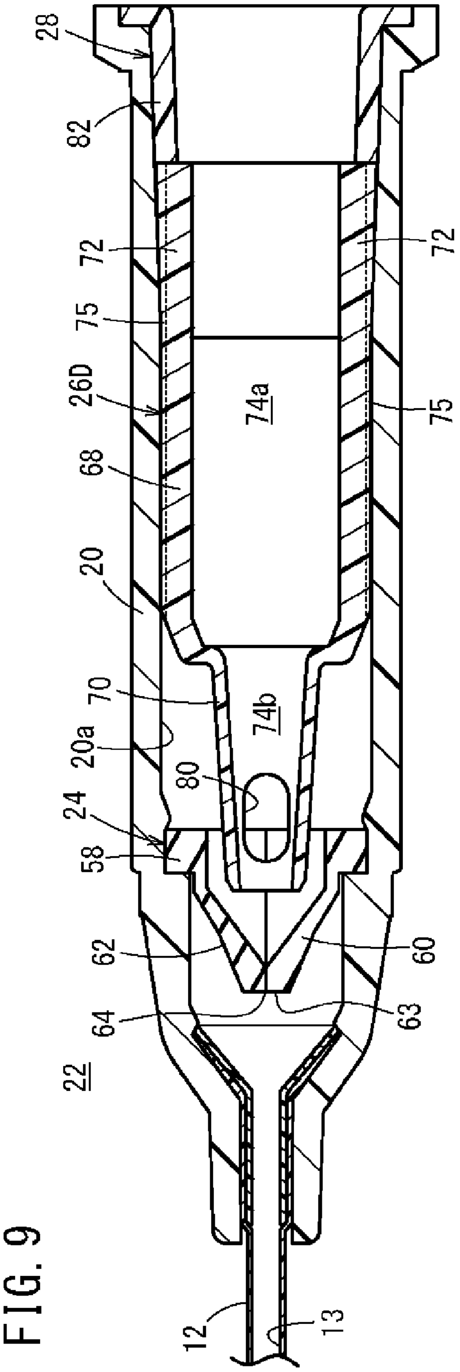
FIG. 9 is a cross-sectional view illustrating a state in which the opening member of FIG. 8A is inserted into a catheter hub according to the third embodiment.

As illustrated in FIG. 9, the rib structure 75 protruding outward from the barrel portion 68 and the foot portion 72 abuts on the inner wall 20*a* to exert a frictional force when the opening member 26D is inserted into the internal space 50 of the catheter hub 20. As a result, the movement of the opening member 26D in the distal direction due to an impact or the like is restricted. That is, the rib structure 75 forms a movement inhibiting mechanism that generates a resistance force against the movement of the opening member 26D to the distal side in the present embodiment.

Incidentally, the frictional force of the rib structure 75 is appropriately set within a range that does not interfere with the connection of the connector 95 to the catheter hub 20. As a result, the opening member 26D can be pressed by the connector 95 to open the valve body 24.

Fourth Embodiment

Figure 10A:
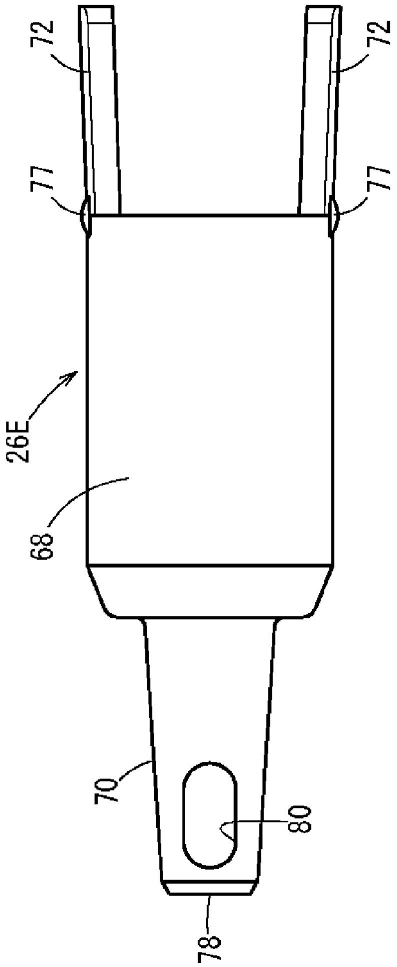
FIG. 10A is a side view of an opening member according to a fourth embodiment.
Figure 10B:
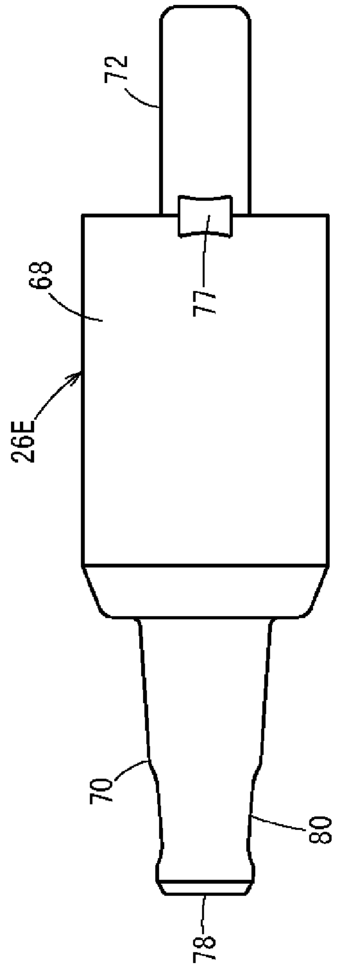
FIG. 10B is a plan view of the opening member of FIG. 10A.

An opening member 26E according to the present embodiment is provided with an island-shaped convex portion 77 (protruding structure) formed so as to protrude outward more than an outer diameter of the barrel portion 68 at a boundary portion between the barrel portion 68 and the foot portion 72 as illustrated in FIGS. 10A and 10B. A pair of the convex portions 77 are provided similarly the foot portions 72, but the present invention is not limited thereto, and only one or a plurality of convex portions 77 may be provided. Further, an installation position of the convex portion 77 is not limited to the boundary portion between the barrel portion 68 and the foot portion 72, and may be provided at an arbitrary position on the outer circumference of the barrel portion 68 or the foot portion 72. Further, a shape of the convex portion 77 is not limited to the island shape, and may be formed in a circular ring shape along the outer circumference of the barrel portion 68, for example.

Figure 11:
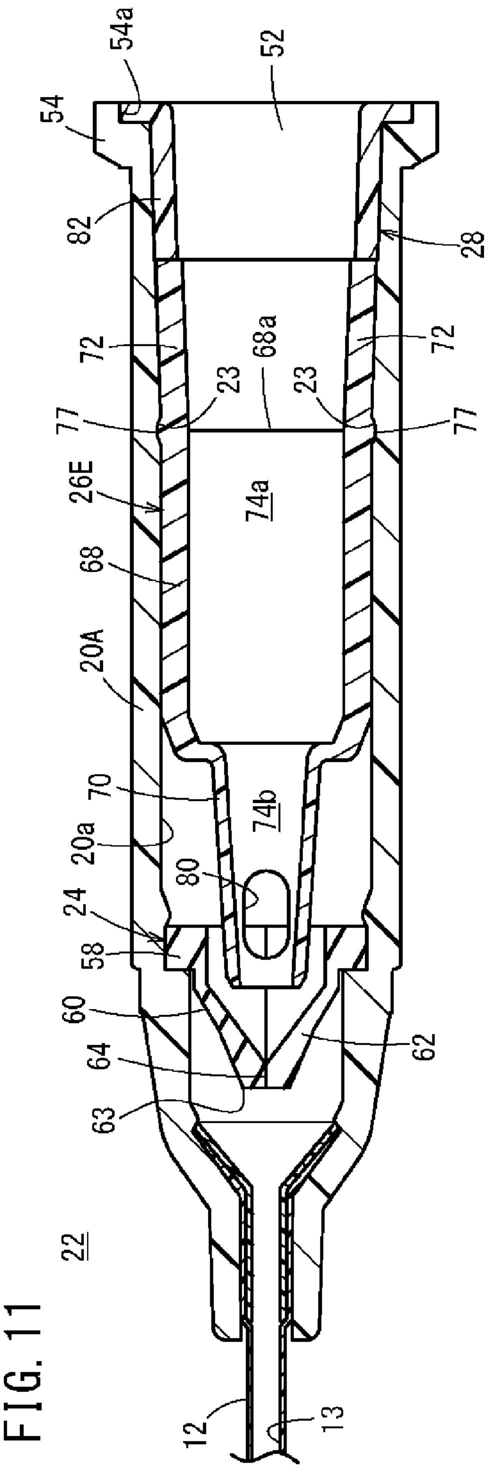
FIG. 11 is a cross-sectional view illustrating a state in which the opening member of FIG. 10A is inserted into a catheter hub according to the fourth embodiment.

As illustrated in FIG. 11, a concave portion 23 to receive the convex portion 77 is formed on the inner wall 20*a* in a portion corresponding to the convex portion 77 of the opening member 26E in a catheter hub 20A of the present embodiment. When the opening member 26E is inserted into the internal space 50 of the catheter hub 20A, the convex portion 77 of the opening member 26E fits into the concave portion 23 of the catheter hub 20, so that a frictional force that restricts the movement of the opening member 26E in the distal direction is exerted. That is, the convex portion 77 of the opening member 26E and the concave portion 23 of the catheter hub 20 form a movement inhibiting mechanism that generates a resistance force against the movement of the opening member 26E to the distal side in the present embodiment.

Incidentally, the frictional force generated by the convex portion 77 and the concave portion 23 is appropriately set within a range that does not interfere with the connection of the connector 95 to the catheter hub 20A. As a result, the opening member 26E can be pressed by the connector 95 to open the valve body 24. Further, the movement inhibiting mechanism may be formed of only the convex portion.

Fifth Embodiment

Figure 12A:
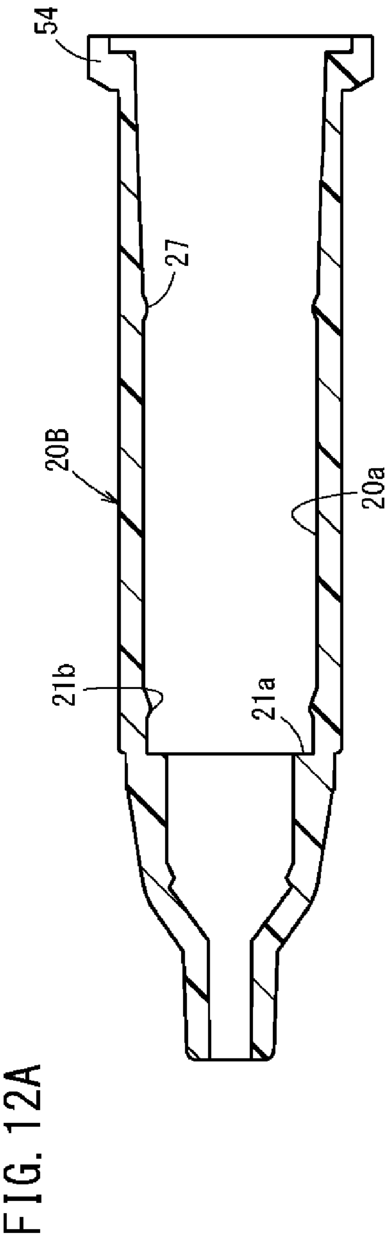
FIG. 12A is a cross-sectional view of a catheter hub according to a fifth embodiment.
Figure 12B:
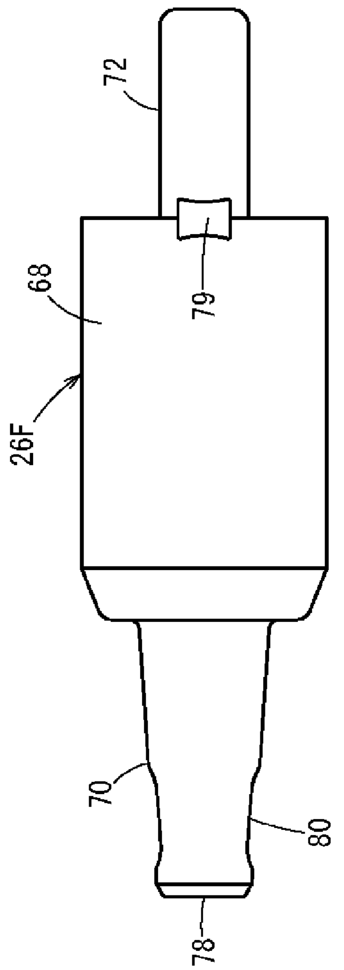
FIG. 12B is a side view of an opening member according to the fifth embodiment.

As illustrated in FIG. 12B, an opening member 26F according to the present embodiment is provided with an island-shaped concave portion 79 that is formed at a boundary portion between the barrel portion 68 and the foot portion 72 to be recessed inward from an outer diameter of the barrel portion 68. A pair of the concave portions 79 are provided similarly the foot portions 72, but the present invention is not limited thereto, and only one or a plurality of concave portions 79 may be provided. Further, an installation position of the concave portion 79 is not limited to the boundary portion between the barrel portion 68 and the foot portion 72, and may be provided at an arbitrary position on the outer circumference of the barrel portion 68 or the foot portion 72. Further, a shape of the concave portion 79 is not limited to the island shape, and may be formed in a circular ring shape along the outer circumference of the barrel portion 68, for example.

As illustrated in FIG. 12A, a convex portion 27 protruding inward is formed on the inner wall 20*a* in a portion corresponding to the concave portion 79 of the opening member 26F in a catheter hub 20B of the present embodiment. A shape of the convex portion 27 is formed in an island shape according to the shape of the concave portion 79. Incidentally, when the concave portion 79 is formed in a circular ring shape, the convex portion 27 may be formed in a circular ring shape.

Figure 13:
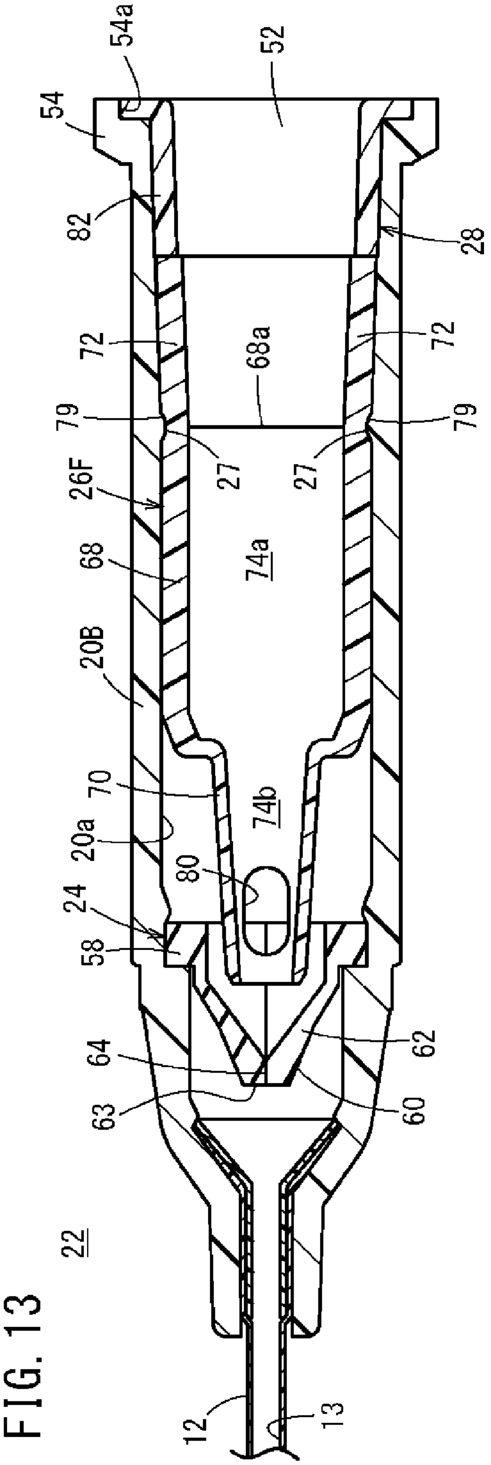
FIG. 13 is a cross-sectional view illustrating a state in which the opening member of FIG. 12B is inserted into the catheter hub of FIG. 12A.

As illustrated in FIG. 13, when the opening member 26F is inserted into the internal space 50 of the catheter hub 20B, the concave portion 79 of the opening member 26F fits into the convex portion 27 of the catheter hub 20B, so that a frictional force that restricts the movement of the opening member 26F in the distal direction is exerted. That is, the concave portion 79 of the opening member 26F and the convex portion 27 of the catheter hub 20B form a movement inhibiting mechanism that generates a resistance force against the movement of the opening member 26F to the distal side in the present embodiment.

Incidentally, the frictional force generated by the concave portion 79 and the convex portion 27 is appropriately set within a range that does not interfere with the connection of the connector 95 to the catheter hub 20B. As a result, the opening member 26F can be pressed by the connector 95 to open the valve body 24. Further, the movement inhibiting mechanism may be formed of only the convex portion.

Although the present invention has been described with reference to the preferred embodiments above, the present invention is not limited to the above-described embodiments, and various modifications can be made within a scope not departing from a gist of the present invention.

The invention claimed is:

1. A catheter assembly comprising:

an inner needle configured to puncture a living body;

a catheter configured to allow the inner needle to be inserted therethrough;

a catheter hub located at a proximal end of the catheter;

a valve body located in an internal space of the catheter hub, the valve body comprising:

an annular portion fixed to an inner wall of the catheter hub, and a valve main body protruding from the annular portion in a distal direction;

an opening member located on a proximal side of the valve body, the opening member comprising:

a cylindrical barrel portion, a neck portion extending from a distal end of the cylindrical barrel portion, wherein a diameter of the neck portion is smaller than a diameter of the cylindrical barrel portion, and first and second ribs protruding outward from the neck portion, wherein the ribs are separated from each other and located on opposite sides of the neck portion, wherein each rib extends along an axial direction from a boundary portion between the cylindrical barrel portion and the neck portion, wherein the first and second ribs are configured to enter an inner diameter portion of the annular portion of the valve body, wherein the opening member is configured to move in the distal direction through the internal space of the catheter hub to open the valve body by inserting the neck portion such that the first and second ribs abut on the valve body.

2. The catheter assembly according to claim 1, wherein the is first and second ribs are configured to generate a frictional force by abutting on the valve body.

3. The catheter assembly according to claim 1, wherein the opening member comprises a foot portion, which is formed so as to widen outward more than an outer diameter of the cylindrical barrel portion and to generate a frictional force by abutting on the catheter hub.

4. The catheter assembly according to claim 1, further comprising a protruding structure that protrudes outward from an outer diameter of the opening member and is configured to generate a frictional force by abutting on the catheter hub.

5. The catheter assembly according to claim 4, wherein the protruding structure comprises a convex portion located on the cylindrical barrel portion or on a foot portion of the opening member.

6. The catheter assembly according to claim 5, wherein a concave portion is formed on an inner wall of the catheter hub in a portion of the catheter hub corresponding to the convex portion.

7. The catheter assembly according to claim 4, wherein the protruding structure comprises a convex portion located at a boundary between the cylindrical barrel portion and the foot portion.

8. The catheter assembly according to claim 1, further comprising a convex portion formed so as to protrude from an inner wall of the catheter hub.

9. The catheter assembly according to claim 8, wherein an outer peripheral portion of the opening member comprises a concave portion in a portion of the opening member corresponding to the convex portion, and the convex portion is fitted into the concave portion to generate a frictional force.

10. The catheter assembly according to claim 1, wherein:

the annular portion of the valve body has a proximal-most end surface facing toward a proximal direction, the opening member comprises a shoulder portion located between the cylindrical barrel portion and the neck portion, the first and second ribs extend along the axial direction from the shoulder portion, and a distal surface of the shoulder portion is configured to abut on the proximal-most end surface of the annular portion of the valve body in an insertion completion state in which a connector is fitted to the catheter hub.

11. The catheter assembly according to claim 1, comprising:

a fixing member located in the internal space of the catheter hub and comprising:

a fixed tubular body having a through-hole configured to penetrate the fixing member, and a notch portion extending in a proximal direction from a distal end of the fixed tubular body.

12. The catheter assembly according to claim 1, wherein:

the annular portion of the valve body has a proximal-most end surface facing toward a proximal direction, and each of the first and second ribs further comprises a distal end surface configured to abut on the proximal-most end surface of the annular portion of the valve body in an initial state.

13. The catheter assembly according to claim 12, wherein:

a distal opening of the opening member is configured to be inserted into the annular portion of the valve body in the initial state.

14. The catheter assembly according to claim 1, wherein:

the valve main body includes a pair of opposite side portions that protrude from the annular portion of the valve body in the distal direction and terminate at an end surface, and the valve body further comprises a slit formed in the valve main body, the slit extending along each of the opposite side portions of the valve main body in a first direction and along the end surface of the valve main body in a second direction that intersects the first direction.

15. A catheter assembly comprising:

an inner needle configured to puncture a living body;

a catheter configured to allow the inner needle to be inserted therethrough;

a catheter hub located at a proximal end of the catheter;

a valve body located in an internal space of the catheter hub, the catheter hub comprising an annular portion;

an opening member located on a proximal side of the valve body, the opening member comprising:

a cylindrical barrel portion, a neck portion extending from a distal end of the cylindrical barrel portion, wherein a diameter of the neck portion is smaller than a diameter of the cylindrical barrel portion, and a foot portion extending from a proximal side of the cylindrical barrel portion, wherein the opening member is configured to move in a distal direction through the internal space of the catheter hub to open the valve body by inserting the neck portion; and first and second ribs that protrude outward from the neck portion beyond an inner diameter of the annular portion of the valve body in a radial direction, wherein the ribs are separated from each other and located on opposite sides of the neck portion, wherein each rib extends along an axial direction from a boundary portion between the cylindrical barrel portion and the neck portion, wherein the first and second ribs are configured to enter an inner diameter portion of the annular portion of the valve body.

16. The catheter assembly according to claim 15, wherein the first and second ribs are separated by 180° in a circumferential direction of the neck portion.

17. A catheter assembly comprising:

an inner needle configured to puncture a living body;

a catheter configured to allow the inner needle to be inserted therethrough;

a catheter hub located at a proximal end of the catheter;

a valve body located in an internal space of the catheter hub;

an opening member located on a proximal side of the valve body, the opening member comprising:

a cylindrical barrel portion, a neck portion extending from a distal end of the cylindrical barrel portion, wherein a diameter of the neck portion is smaller than a diameter of the cylindrical barrel portion, and a foot portion extending from a proximal side of the cylindrical barrel portion, the foot portion being formed so as to widen outward more than an outer diameter of the cylindrical barrel portion, and first and second ribs protruding outward from the neck portion, wherein the ribs are separated from each other and located on opposite sides of the neck portion, wherein each rib extends along an axial direction from a boundary portion between the cylindrical barrel portion and the neck portion, wherein the first and second ribs are configured to enter an inner diameter portion of the valve body, wherein the opening member is configured to move in a distal direction through the internal space of the catheter hub to open the valve body by inserting the neck portion such that the first and second ribs abut on the valve body.

* * * * *